(12) United States Patent
Kiyota

(10) Patent No.: US 12,203,063 B2
(45) Date of Patent: Jan. 21, 2025

(54) STIRRING METHOD, CELL CULTURE METHOD, STIRRING APPARATUS, AND CELL CULTURE APPARATUS

(71) Applicant: NIKON CORPORATION, Tokyo (JP)

(72) Inventor: Yasujiro Kiyota, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 360 days.

(21) Appl. No.: 17/004,103

(22) Filed: Aug. 27, 2020

(65) Prior Publication Data

US 2020/0392443 A1 Dec. 17, 2020

Related U.S. Application Data

(60) Division of application No. 13/401,051, filed on Feb. 21, 2012, now abandoned, which is a continuation of application No. PCT/JP2010/005414, filed on Sep. 2, 2010.

(30) Foreign Application Priority Data

Sep. 3, 2009 (JP) ................................. 2009-203745

(51) Int. Cl.
*C12M 1/00* (2006.01)
*C12M 1/26* (2006.01)
*C12M 1/34* (2006.01)
*C12M 1/36* (2006.01)
*C12M 3/06* (2006.01)

(52) U.S. Cl.
CPC ............ *C12M 27/16* (2013.01); *C12M 33/08* (2013.01); *C12M 41/14* (2013.01); *C12M 41/36* (2013.01); *C12M 41/42* (2013.01); *C12M 41/48* (2013.01)

(58) Field of Classification Search
CPC ...... C12M 27/16; C12M 33/08; C12M 41/14; C12M 41/36; C12M 41/42; C12M 41/48
See application file for complete search history.

(56) References Cited

U.S. PATENT DOCUMENTS

| 5,573,942 | A | 11/1996 | Miyamoto |
| 6,673,532 | B2 * | 1/2004 | Rao ......................... C12M 41/26 |
| 6,673,595 | B2 | 1/2004 | Barbera-Guillem |
| 2003/0054335 | A1 | 3/2003 | Taya et al. |
| 2005/0170491 | A1 | 8/2005 | Takagi et al. |
| 2008/0293131 | A1 * | 11/2008 | Nakamura ............. C12M 23/50 |
| | | | 435/289.1 |

(Continued)

FOREIGN PATENT DOCUMENTS

| EP | 1 900 806 A1 | 3/2008 |
| JP | S58-155087 A | 9/1983 |

(Continued)

OTHER PUBLICATIONS

Dec. 5, 2016 Office Action issued in U.S. Appl. No. 13/401,051.
Apr. 24, 2017 Office Action issued in European Patent Application No. 10813514.6.

(Continued)

*Primary Examiner* — Liban M Hassan
(74) *Attorney, Agent, or Firm* — Oliff PLC

(57) ABSTRACT

A stirring apparatus including a stirring mechanism configured to execute a stirring process on cells in a culture vessel, and a control unit programmed to at least one of control the stirring mechanism, determine the stirring process of the stirring mechanism, and determine whether the stirring process is performed or not.

7 Claims, 10 Drawing Sheets

(56) References Cited

U.S. PATENT DOCUMENTS

2009/0081769 A1 3/2009 Kiyota et al.
2009/0304257 A1 12/2009 Ohjo et al.

FOREIGN PATENT DOCUMENTS

| JP | H05-168471 A | | 7/1993 | |
| --- | --- | --- | --- | --- |
| JP | 09145725 A | * | 6/1997 | |
| JP | 2004-16194 A | | 1/2004 | |
| WO | WO-2007105363 A1 | * | 9/2007 | ............ C12M 23/50 |
| WO | 2007/119764 A1 | | 10/2007 | |

OTHER PUBLICATIONS

Jun. 10, 2016 Search Report issued in European Patent Application No. 10813514.6.
Aug. 17, 2017 Office Action issued in U.S. Appl. No. 13/401,051.
Dec. 11, 2017 Office Action issued in European Patent Application No. 10 813 514.6.
Aug. 2, 2018 Office Action issued in U.S. Appl. No. 13/401,051.
Oct. 3, 2019 Office Action issued in U.S. Appl. No. 13/401,051.
Apr. 16, 2020 Quayle Action issued in U.S. Appl. No. 13/401,051.
Jul. 6, 2020 Notice of Allowance issued in U.S. Appl. No. 13/401,051.
Reyes, et al., "A centrifugation cell adhesion assay for high-throughput screening of biomaterial surfaces", J. Biomed. Mater. Res. Part A, (2003), vol. 67A, No. 1, pp. 328-333.
Oct. 5, 2010 International Search Report issued in International Application No. PCT/JP2010/005414.
Dec. 4, 2014 Office Action issued in U.S. Appl. No. 13/401,051.
Jun. 18, 2013 Office Action issued in U.S. Appl. No. 13/401,051.
Sep. 4, 2015 Office Action issued in U.S. Appl. No. 13/401,051.
Mar. 10, 2014 Office Action issued in U.S. Appl. No. 13/401,051.
Feb. 21, 2019 Office Action issued in U.S. Appl. No. 13/401,051.

* cited by examiner

STIRRING METHOD, CELL CULTURE METHOD, STIRRING APPARATUS, AND CELL CULTURE APPARATUS

CROSS REFERENCE TO RELATED APPLICATION

This application is a Divisional of application Ser. No. 13/401,051, filed on Feb. 21, 2012, which is a continuation application of International Application No. PCT/JP2010/005414, filed on Sep. 2, 2010, designating the U.S., in which the International Application claims a priority date of Sep. 3, 2009, based on prior filed Japanese Patent Application No. 2009-203745, the entire contents of which are incorporated herein by reference.

BACKGROUND

1. Field

The present application relates to a stirring method, a cell culture method, a stirring apparatus and a cell culture apparatus used at a time of culturing cells.

2. Description of the Related Art

When culturing cells, a work of replacing a medium inside of a culture vessel and a work of seeding cells to be cultured in a new medium are required. Such works are often carried out by hand by a skilled worker, by taking complication of the works and suppression of occurrence of contamination and the like into consideration. Recently, there has been conducted a culture using stem cells for regenerative medicine, and when such culture of cells is conducted by hand, efficiency regarding the culture of cells is poor. In recent years, there has been provided a cell culture apparatus which realizes an improvement in efficiency associated with a culture of cells by automatically executing the aforementioned works (refer to Patent Document 1: Japanese Unexamined Patent Application Publication No. 2004-016194).

It has been clear that, when culturing cells by using the cell culture apparatus as described above, an adhesive strength between a cell and an inner surface (referred to as a surface for adhesion, hereinafter) such as a bottom surface of a culture vessel to which the cell is adhered, and a relation between the adhesive strength between the cell and the surface for adhesion and an adhesive strength between respective cells exert large influence on the culture of cells. For this reason, depending on a combination of a cell to be cultured and a culture vessel used at the time of performing the culture, a density variation of cells proliferated in a process of performing the culture occurs. The occurrence of variation as above becomes a main cause of preventing the cells to be cultured from being efficiently proliferated.

The present application has a proposition to provide a stirring method, a cell culture method, a stirring apparatus and a cell culture apparatus capable of efficiently culturing cells to be cultured, by preventing a density variation of cells that occurs in a process of performing the culture.

SUMMARY

A stirring method includes measuring, with respect to cells which adhere to an inner surface of a culture vessel to be cultured, an ease of peeling between the culture vessel and the cell and an ease of peeling between the mutual cells, and performing a stirring process on the cells in the culture vessel by determining a process content of the stirring process with respect to the cells in the culture vessel, based on the ease of peeling between the culture vessel and the cell and an ease of peeling between the mutual cells.

Further, a cell culture method includes seeding the cells in the culture vessel, and stirring the cells cultured in the culture vessel, by using the stirring method.

Further, the measuring measures the ease of peeling between the culture vessel and the cell and the ease of peeling between the mutual cells includes measuring the ease of peeling between the culture vessel and the cell by transporting the culture vessel at a predetermined acceleration and stopping the culture vessel, when the cells are seeded in the culture vessel and the cells are fixed to the culture vessel, and measuring the ease of peeling between the mutual cells by transporting the culture vessel at a predetermined acceleration and stopping the culture vessel after the cells are cultured in the culture vessel.

Further, a stirring apparatus includes a stirring unit executing a stirring process on cells which adhere to an inner surface of a culture vessel to be cultured, a stirring process content determining unit determining a process content of the stirring process in the stirring unit, in accordance with a magnitude relation between an ease of peeling between the cell and the inner surface of the culture vessel and an ease of peeling between the mutual cells, and a control unit drive-controlling the stirring unit based on the process content of the stirring process determined by the stirring process content determining unit.

Further, there is provided an input unit inputting a type of the culture vessel and a type of the cell, and the stirring process content determining unit estimates the magnitude relation based on the type of the culture vessel and the type of the cell input by the input unit, and determines the content of the stirring process in the stirring unit.

Further, there is provided a storage unit storing stirring process information to which the process content of the stirring process is corresponded, in accordance with the type of the culture vessel and the type of the cell, and the stirring process content determining unit determines the process content of the stirring process in the stirring unit by refereeing to the stirring process information when the type of the culture vessel and the type of the cell are input by the input unit.

Further, it is preferable that there are provided a culture vessel transporting unit giving an acceleration to the culture vessel, an observing unit observing movements of cells in the culture vessel, and an analyzing unit determining the magnitude relation by analyzing an observation result of the cells obtained by the observing unit.

Further, it is preferable that the magnitude relation is determined as a magnitude relation between an adhesive strength between the cell and the inner surface of the culture vessel and an adhesive strength between the mutual cells.

Further, it is preferable that the magnitude relation is determined as a magnitude relation between a moving distance when the cell adhered to the culture vessel is peeled off from the culture vessel when applying the acceleration and a moving distance of the cell of the mutually adhered cells when the mutual cells are peeled off from each other.

Note that it is preferable that the process content of the stirring process is formed of the presence/absence of the stirring process, the acceleration given to the culture vessel when executing the stirring process and a number of times of giving the acceleration.

Further, a cell culture apparatus includes any one of the stirring apparatuses, and a temperature-controlled room including the stirring apparatus in an inside thereof and maintaining an environment to a state of culturing the cells.

Further, a stirring apparatus includes a stirring unit executing a stirring process with respect to cells which adhere to an inner surface of a culture vessel to be cultured, an input unit inputting a type of the culture vessel and a type of the cell, a storage unit storing a process content of the stirring process determined based on previously determined ease of peeling between the culture vessel and the cell and ease of peeling between the mutual cells from a combination of the type of the culture vessel and the type of the cell input by the input unit, and a control unit drive-controlling the stirring unit based on the process content of the stirring process read from the storage unit based on the type of the culture vessel and the type of the cell.

Further, a cell culture apparatus includes the stirring apparatus, and a temperature-controlled room including the stirring apparatus in an inside thereof and maintaining an environment to a state of culturing the cells.

According to the present embodiment, it is possible to efficiently culture cells to be cultured by preventing an occurrence of density variation of the cells.

DETAILED DESCRIPTION OF THE EMBODIMENTS

Figure 1:
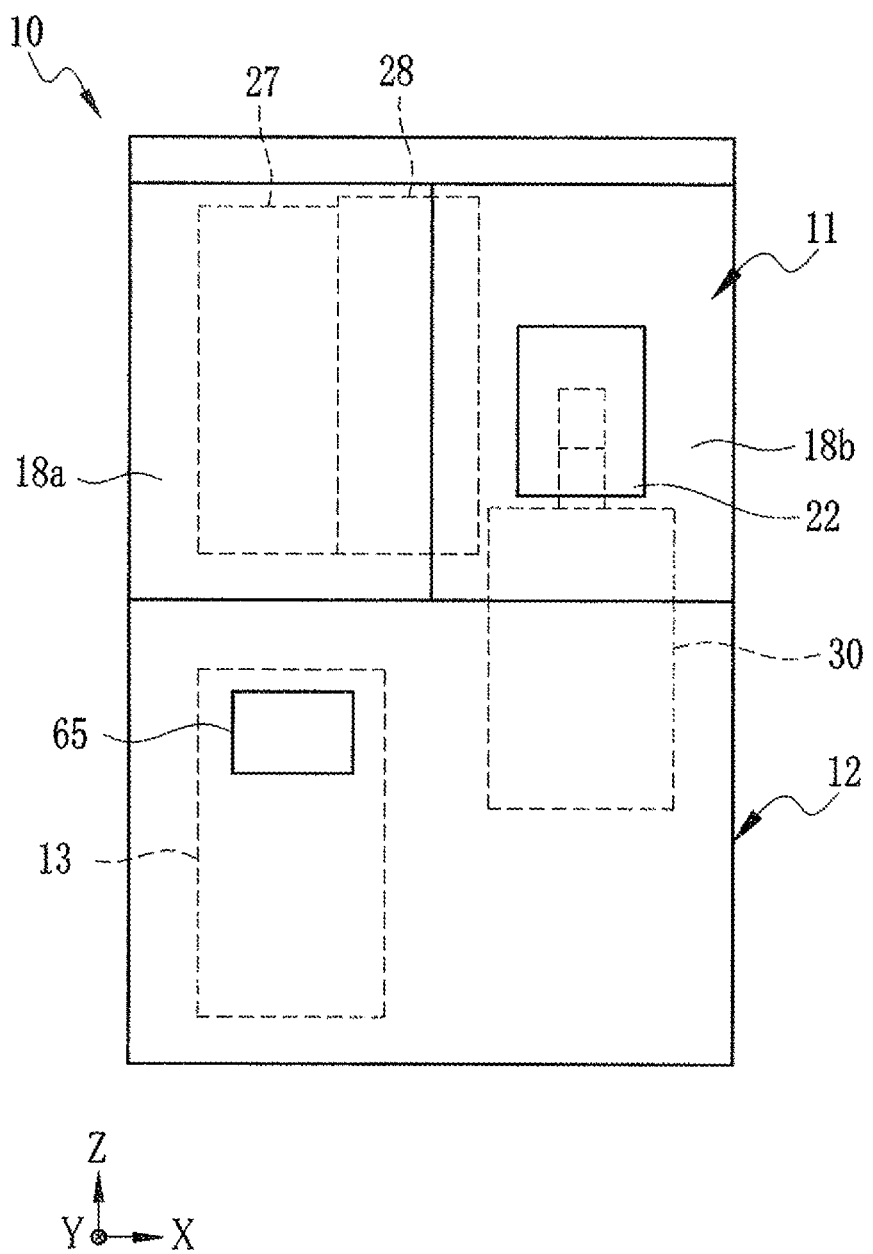
FIG. 1 is a front view illustrating an outline of a cell culture apparatus.
Figure 2:
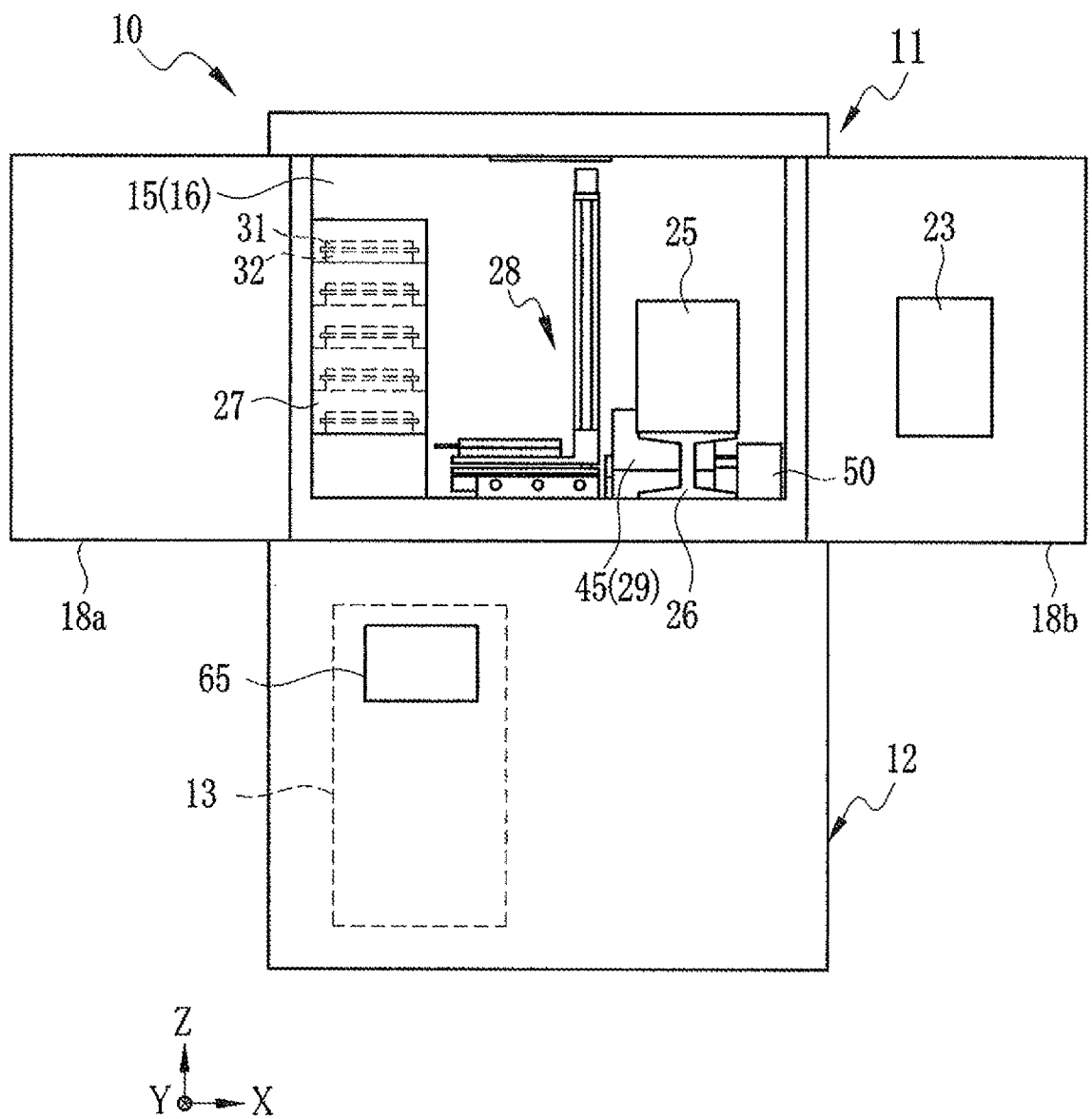
FIG. 2 is a front view illustrating an outline of the cell culture apparatus whose outer door is opened.
Figure 3:
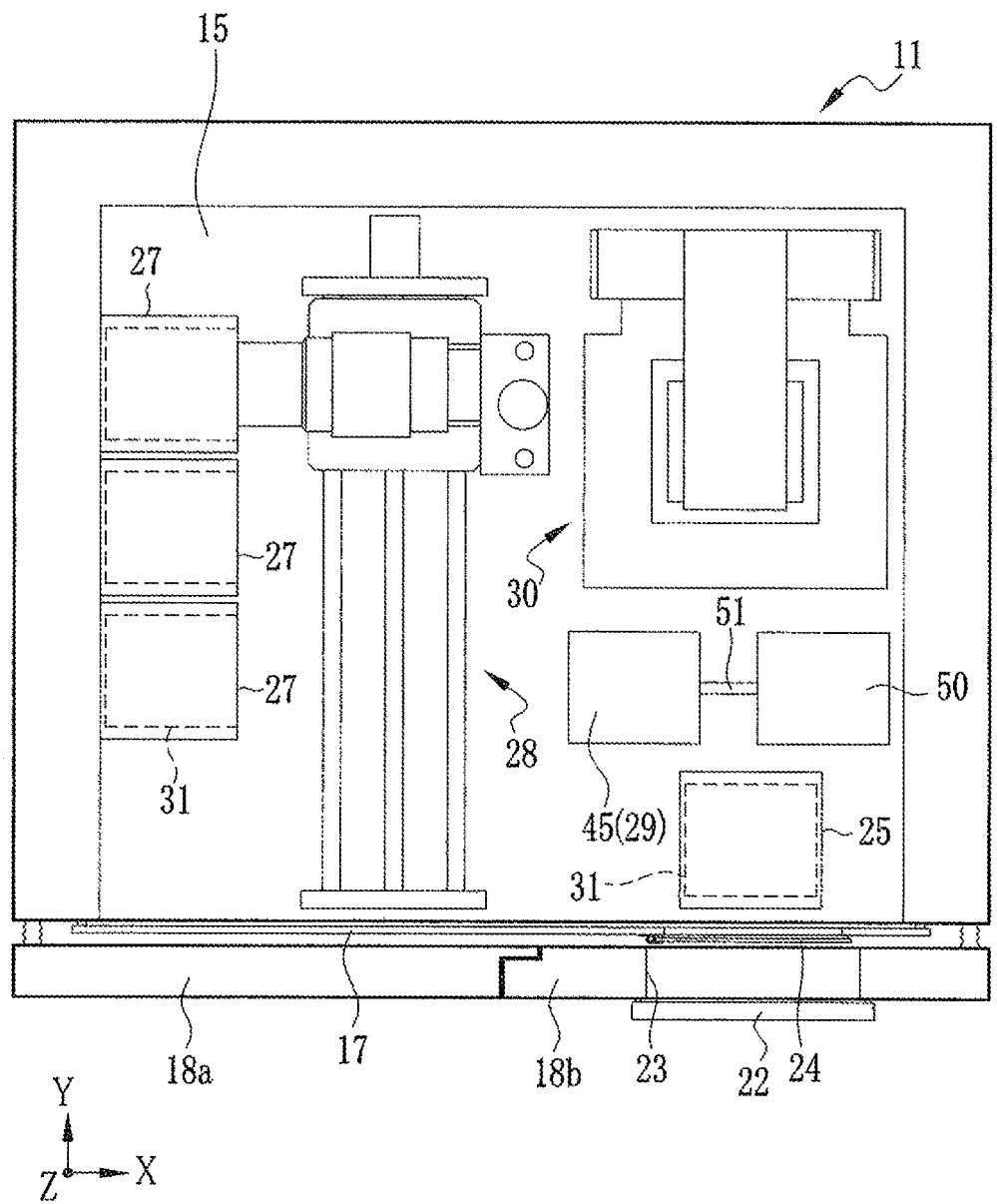
FIG. 3 is a schematic diagram illustrating a configuration of an interior of a temperature-controlled room.

Hereinafter, a configuration of a cell culture apparatus of the present embodiment will be described in detail. Note that the cell culture apparatus described hereinbelow is an example, and the present invention is not limited to the configuration of the cell culture apparatus described in the present embodiment. As illustrated in FIG. 1 to FIG. 3, a cell culture apparatus 10 includes a first casing 11 in which a sample such as a microorganism and a cell is cultured, and a second casing 12 housing a control unit 13. In an assembly state of the cell culture apparatus 10, the first casing 11 is disposed on an upper portion of the second casing 12.

The first casing 11 includes a temperature-controlled room 15 in which an inside thereof is covered by a heat insulating material. The temperature-controlled room 15 is connected with an outside by a front opening 16 formed on a front surface of the first casing 11. The front opening 16 of the first casing 11 is closed by an inner door 17 and two outer doors 18a, 18b. A packing or the like is provided to a peripheral edge portion of a rear surface side of the inner door 17 and the outer doors 18a, 18b, and when respective doors are closed, the inside of the temperature-controlled room 15 is maintained in an air-tight state. Specifically, when only the inner door 17 is closed, or when not only the inner door 17 but also the two outer doors 18a, 18b are respectively closed, the inflow of heat into the inside of the temperature-controlled room 15 from the outside of the cell culture apparatus 10 and the outflow of heat to the outside of the cell culture apparatus 10 from the inside of the temperature-controlled room 15 are prevented. Note that the inside of the temperature-controlled room 15 is controlled to have previously set environmental conditions (temperature, humidity, carbon dioxide concentration and the like) by a temperature adjusting device, an atomizing device and the like whose illustration is omitted.

Out of the aforementioned outer doors 18a, 18b, the outer door 18b is provided with a carry-in door 22. The carry-in door 22 is opened when a carrier 25 housing a culture vessel 31 is carried in a carrier installation cradle 26, or when the carrier 25 installed on the carrier installation cradle 26 is carried out. When the carry-in door 22 is opened, a small door 24 provided to the inner door 17 via an opening 23 is exposed. The inner door 17 and the small door 24 are formed of a glass or a transparent synthetic resin, and it is designed such that even when the outer doors 18a, 18b are opened, environmental conditions inside of the doors are not changed suddenly. By opening the small door 24 provided to the inner door 17, it becomes possible to carry the carrier 25 housing the culture vessel 31 in the carrier installation cradle 26, or to carry out the carrier 25 installed on the carrier installation cradle 26. Note that the carrier 25 can house three culture vessels 31 one above the other with a predetermined space therebetween, for example.

There are disposed, in the inside of the temperature-controlled room 15, the carrier installation cradle 26, a container 27, a vessel transport mechanism 28, a stirring mechanism 29, an observation unit 30 and the like. Note that although the illustration is omitted, there are disposed, in the inside of the temperature-controlled room 15, a medium replacement mechanism that performs medium replacement, a seeding mechanism that performs seeding of cells, and the like.

As described above, the carrier 25 is placed on an upper portion of the carrier installation cradle 26. Although the illustration is omitted, a guide rail is provided to a side surface of the carrier installation cradle 26. The guide rail is fitted into a guide groove provided, on a lower surface of the carrier 25, with a space into which the guide rail is fitted, thereby regulating a moving direction of the carrier 25 to be carried in or carried out. Note that an extending direction of the guide groove is orthogonal to a direction in which the culture vessel 31 is carried in the carrier 25 or a direction in which the culture vessel 31 is carried out of the carrier.

The container 27 is disposed on the left side of the temperature-controlled room 15 when seen from the front of the first casing 11. The container 27 has a plurality of shelves in a longitudinal direction, and the culture vessel 31 is housed in each of the shelves. Note that in the container 27, positions at which the respective culture vessels 31 are housed (referred to as housing positions, hereinafter) are previously set. To each of the housing positions, an identification number for distinguishing between one housing position and another housing position is corresponded, and based on the identification number, an observation schedule of cells to be cultured, image data obtained at the time of the observation and the like are collectively managed.

As the culture vessel 31 placed in the container 27, a dish, a well plate, a flask or the like can be cited. In each of the culture vessels 31, a sample to be a culture object such as a cell is held together with a medium being a culture solution 33. These culture vessels 31 are handled in a state of being positioned and fixed to transparent tray-shaped holders 32 when performing the culture of cells and the observation of cells by the cell culture apparatus 10. Note that as the cell, there can be cited a cell utilized for regenerative medicine such as a stem cell, for example.

The vessel transport mechanism 28 is disposed substantially on a center of the temperature-controlled room 15 when seen from the front of the first casing 11. The vessel transport mechanism 28 transports the culture vessel 31 housed in the carrier 25 toward the container 27 (or from the container 27), or it transports the culture vessel 31 housed in the container 27 toward any one of the carrier 25, the observation unit 30 and the stirring mechanism 29 (or from any one of the carrier 25, the observation unit 30 and the stirring mechanism 29). Positions of respective parts in the vessel transport mechanism 28 are monitored by the control unit 13 via an encoder or the like.

The stirring mechanism 29 is provided to eliminate a seeding variation which occurs at the time of seeding the cells to be cultured in the culture vessel 31, and a density variation of cells which occurs in a process of culturing the cells seeded in the culture vessel 31. Note that a stirring process performed by the stirring mechanism 29 corresponds to a process in which at least any one of a vibration in an X direction, a vibration in a Y direction, and a vibration in a rotational direction in which a straight line L is set as a center, which will be described later, or a combination of these vibrations is applied a predetermined number of times to the cells in the medium together with the culture vessel 31. Hereinafter, explanation will be made by setting such that, among the cells cultured in the culture vessel 31, a cell adhered to a bottom surface (referred to as a surface for adhesion, hereinafter) of the culture vessel 31 or a cell connected (adhered) to another cell is called as an adhered cell, and a cell which is not adhered to the surface for adhesion and is suspended in the culture solution 33 is called as a suspended cell.

Figure 4:
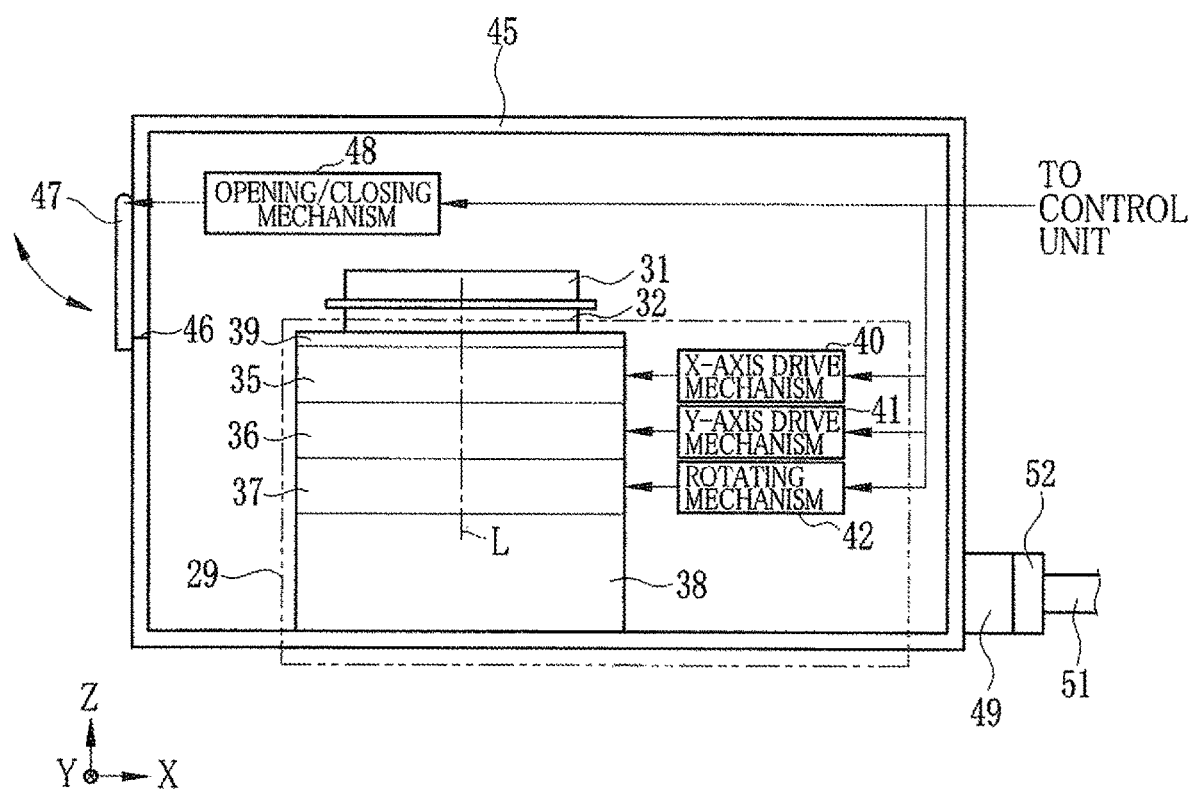
FIG. 4 is a schematic diagram illustrating a configuration of a stirring apparatus.

As illustrated in FIG. 4, the stirring mechanism 29 includes an X stage 35, a Y stage 36, a rotation stage 37, and a base 38. The X stage 35 is disposed on an uppermost portion of the stirring mechanism 29, and to an upper surface thereof, a plate 39 that performs positioning of the culture vessel 31 is attached. The holder 32 fixing the culture vessel 31 is positioned and fixed to an upper surface of the plate 39. The X stage 35 is moved in an X-axis direction by an X-axis drive mechanism 40.

The Y stage 36 is disposed between the X stage 35 and the rotation stage 37. The Y stage 36 is moved in a Y-axis direction by a Y-axis drive mechanism 41. When the Y stage 36 moves in the Y-axis direction, the X stage 35 also moves in the Y-axis direction together with the Y stage 36.

The rotation stage 37 is disposed between the Y stage 36 and the base 38. The rotation stage 37 is rotated around the straight line L illustrated in FIG. 4 by a rotating mechanism 42. The X stage 35 and the Y stage 36 also rotate together with the rotation of the rotation stage 37.

Note that in FIG. 4, in order to eliminate complication of drawing, a configuration in which the X-axis drive mechanism 40, the Y-axis drive mechanism 41, and the rotating mechanism 42 are disposed on the outside of the X stage 35, the Y stage 36, the rotation stage 37, and the base 38, is employed, but, it is assumed that the mechanisms are actually disposed on the inside of the stirring mechanism 29. Each of the aforementioned X-axis drive mechanism 40, Y-axis drive mechanism 41, and rotating mechanism 42 is drive-controlled via the later-described control unit 13. Control contents at the time of driving these mechanisms (an intensity level at the time of performing stirring, the number of times of stirring and the like) are determined based on a type of cell cultured in the culture vessel 31, a type of culture vessel 31 used at the time of performing the culture, and the like.

The stirring mechanism 29 is housed inside of an anti-scattering case 45. The anti-scattering case 45 prevents, when the culture solution 33 (including cells in the culture solution 33) is scattered from a gap generated in the culture vessel 31, the solution from being scattered to another mechanism in the temperature-controlled room 15. An opening is provided to a bottom surface of the anti-scattering case 45, and through the opening, a connector (illustration is omitted) of the stirring mechanism 29 is inserted. The connector is connected to a connector provided to a bottom surface of the temperature-controlled room 15 when the stirring mechanism 29 is disposed at a predetermined position in the temperature-controlled room 15. Note that although the illustration is omitted, a weight sensor whose illustration is omitted is built in the stirring mechanism 29, and the sensor measures a weight of the culture vessel 31 before and after the stirring process performed by the stirring mechanism 29. Note that the measured result is output to the later-described control unit 13, and when the control unit 13 determines that a change in weight of the culture vessel 31 occurs, an alarm display is made on a later-described display unit 65a. In such a case, the anti-scattering case 45 is detached together with the stirring mechanism 29, and is replaced with new one.

Further, to an upper portion of a side surface facing the vessel transport mechanism 28 among side surfaces of the anti-scattering case 45, an opening 46 is provided. By providing the opening 46, it becomes possible to carry the culture vessel 31 transported by the vessel transport mechanism 28 in the stirring mechanism 29 disposed inside of the anti-scattering case 45, or to carry out the culture vessel 31 positioned in the stirring mechanism 29 to the outside of the anti-scattering case 45.

An introduction door 47 is provided to the anti-scattering case 45 so that it can freely pivot between a position at which the opening 46 is shielded (shielding position) and a position at which the opening is exposed (exposing position). The introduction door 47 is normally kept at the shielding position. When the culture vessel 31 after being subjected to the stirring process by the stirring mechanism 29 is carried out to the outside of the anti-scattering case 45 or when the culture vessel 31 on which the stirring process is to be performed is carried in the inside of the anti-scattering case 45 to place the vessel on the stirring mechanism 29, the introduction door 47 is pivoted from the shielding position to the exposing position by an opening/closing mechanism 48.

To the side surface on the opposite side of the side surface of the anti-scattering case 45 to which the opening 46 is provided, a connector 49 is provided. To the connector 49, a connector 52 provided to one end of a tube 51 of a compressor 50 (refer to FIG. 2) is fitted. The compressor 50 operates when the culture solution 33 scatters from the culture vessel 31 in a process of performing the stirring process, and sets an air pressure inside of the anti-scattering case 45 to be lower than an air pressure inside of the temperature-controlled room 15. By setting the air pressure inside of the anti-scattering case 45 to be lower than the air pressure inside of the temperature-controlled room 15, the culture solution 33 scattered to the inside of the anti-scattering case 45 is prevented from being leaked to the outside of the anti-scattering case 45 from the inside of the anti-scattering case 45.

A main body of the observation unit 30 is placed inside of the second casing 12, and an upper portion of the observation unit 30 is disposed so as to be inserted from a lower part to an inner part of the first casing 11. When seen from the front of the first casing 11, the observation unit 30 is disposed on the right side of the temperature-controlled room 15. The observation unit is disposed by being fitted into an opening on a bottom surface of the first casing 11. Note that although the configuration of the observation unit 30 will be omitted, as the observation unit 30, there can be cited a microscope capable of performing an observation method of a phase difference observation, a fluorescence observation, a differential interference observation or the like.

The observation unit 30 performs the phase difference observation on the culture vessel 31 housed in the carrier 25 immediately after the carrier is installed on the carrier installation cradle 26, or the culture vessel 31 when a fixing time has elapsed after housing the vessel in the container 27, for example, thereby obtaining an entire image of the culture vessel 31 or an image of cells to be cultured. Here, the fixing time corresponds to a period of time during which the suspended cell in the culture solution 33 is adhered to the surface for adhesion, for example, and is 2 hours, for instance. Image data obtained by the observation unit 30 is stored in a later-described database unit 72.

Figure 5:
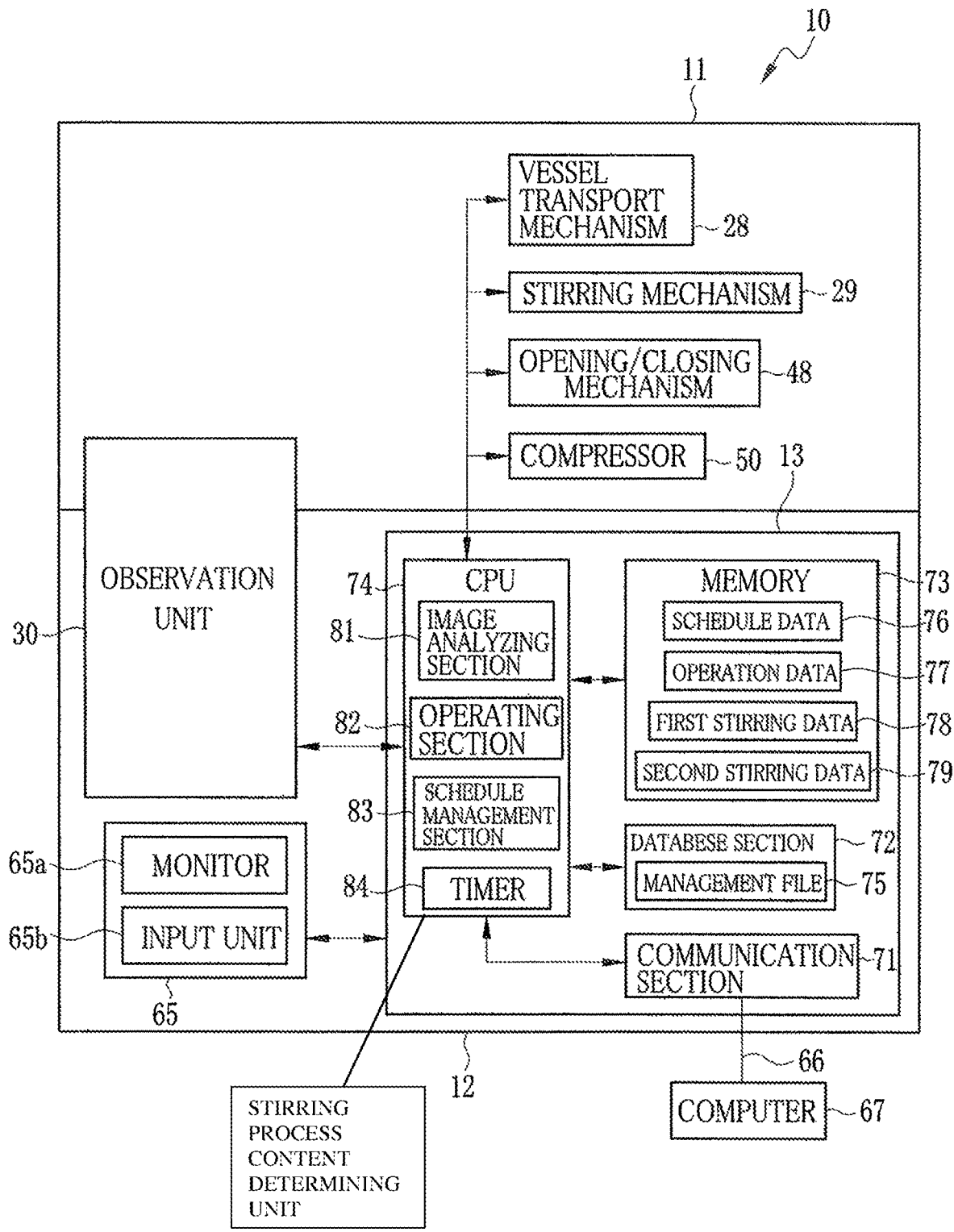
FIG. 5 is a functional block diagram illustrating an electrical configuration of the cell culture apparatus.

Next, an electrical configuration of the cell culture apparatus 10 of the present embodiment will be described. As illustrated in FIG. 5, the second casing 12 houses the main body portion of the observation unit 30 described above, and the control unit 13. Further, on a front surface of the second casing 12, an operation panel 65 including a monitor 65a and an input unit 65b is disposed. Note that as the input unit 65b, there can be cited a keyboard, a mouse or the like. To the control unit 13, it is also possible to connect a computer 67 via a communication line 66.

The control unit 13 is connected to the vessel transport mechanism 28, the stirring mechanism 29, the opening/closing mechanism 48, the observation unit 30, the compressor 50, and the monitor 65a and the input unit 65b of the operation panel 65, respectively. The control unit 13 comprehensively controls respective parts of the cell culture apparatus 10 in accordance with a predetermined program. As an example, the control unit 13 automatically determines an observation schedule based on a type of the cell and a type of the culture vessel 31 used at the time of performing the culture, input through an operation of the input unit 65b of the operation panel 65 or an operation of the computer 67. Further, the control unit 13 automatically executes an observation sequence for the culture vessel 31 based on the determined observation schedule. Note that the observation schedule includes not only a schedule for performing observation of cells cultured in the culture vessel 31 and a schedule for performing medium replacement, but also a schedule of the stirring process in the stirring mechanism 29 and the like.

The control unit 13 has a communication section 71, the database section 72, a memory 73, and a CPU 74. Note that each of the communication section 71, the database section 72, and the memory 73 is connected to the CPU 74. The communication section 71 executes transmission and reception of data to and from the computer 67 disposed on the outside of the cell culture apparatus 10 via a wireless or wired communication line.

In the database section 72, history information regarding environmental conditions (temperature, humidity, carbon dioxide concentration and the like) inside of the temperature-controlled room 15, the image data obtained by the observation unit 30 and the like are stored. Note that each of these pieces of data is preferably stored as a management file 75 to which an identification number allocated to each of the culture vessels 31 is corresponded.

In the memory 73, schedule data 76 of the observation sequence described above, and operation data 77 for calculating an operator at the time of executing the observation sequence are recorded. The schedule data 76 is data based on the observation schedule. When the stirring process is not included in the observation schedule, for example, the schedule data 76 is formed of data indicating a start time and a time required for observation in each observation process, a start time of the medium replacement process and a time required for the replacement process, and image-capturing conditions in the observation unit 30. On the other hand, the schedule data 76 when the stirring process is included as the observation schedule is formed of data, in addition to the aforementioned data, based on a schedule regarding the stirring process such as data for specifying a start time of the stirring process, a time required for the stirring process, stirring conditions (the intensity at the time of the stirring and the number of times of stirring) of the stirring process in the stirring mechanism 29. The schedule data 76 is stored by being corresponded to the aforementioned identification number, for example. Since the schedule data 76 is only required to be managed by being corresponded to the management file 75, it may be stored in the memory 73, separately from the management file 75, or may also be stored in the management file 75 stored in the database section 72.

Further, in the memory 73, not only the aforementioned schedule data 76 and operation data 77 but also first stirring data 78 and second stirring data 79 are stored. The first stirring data 78 is read when the type of the cell and the type of the culture vessel 31 are input through the operation of the input unit 65b. The first stirring data 78 is data in which an adhesive strength between a cell and a cell and an adhesive strength between a cell and a surface for adhesion, the presence/absence of the stirring process, and an intensity level (intensity of stirring) and the number of times of stirring at the time of the stirring, are respectively corresponded to a combination of the type of the cell and the type of the culture vessel 31. Note that as the intensity level at the time of the stirring, there can be cited an acceleration applied to each of the stages when the X stage 35 or the Y stage 36 provided to the stirring mechanism 29 are vibrated or when the rotation stage 37 is rotated. Further, the number of times of stirring corresponds to the number of times of vibrating each stage, in other words, the number of times of applying the acceleration.

The second stirring data 79 is used at the time of executing a later-described measurement mode. The second stirring data 79 is formed of a combination of an adhesive strength generated between a cell and a cell when the cells are connected to each other and an adhesive strength between a cell and a culture vessel generated when the cell is adhered to a surface for adhesion, and data to which the presence/absence of the stirring process, the intensity level of the stirring, and the number of times of stirring are corresponded, obtained as a result of comparing these adhesive strengths.

The CPU 74 is a processor that executes various types of operation process in the control unit 13. The CPU 74 has functions of an image analyzing section 81, an operating section 82, a schedule management section 83 and a timer 84. The image analyzing section 81 executes image analysis by using the image data obtained by the observation unit 30. The operating section 82 executes operation associated with the image analysis. The schedule management section 83 performs a registration process and a changing process of the observation schedule. Further, the timer 84 is used at the time of managing the observation schedule.

Figure 6:
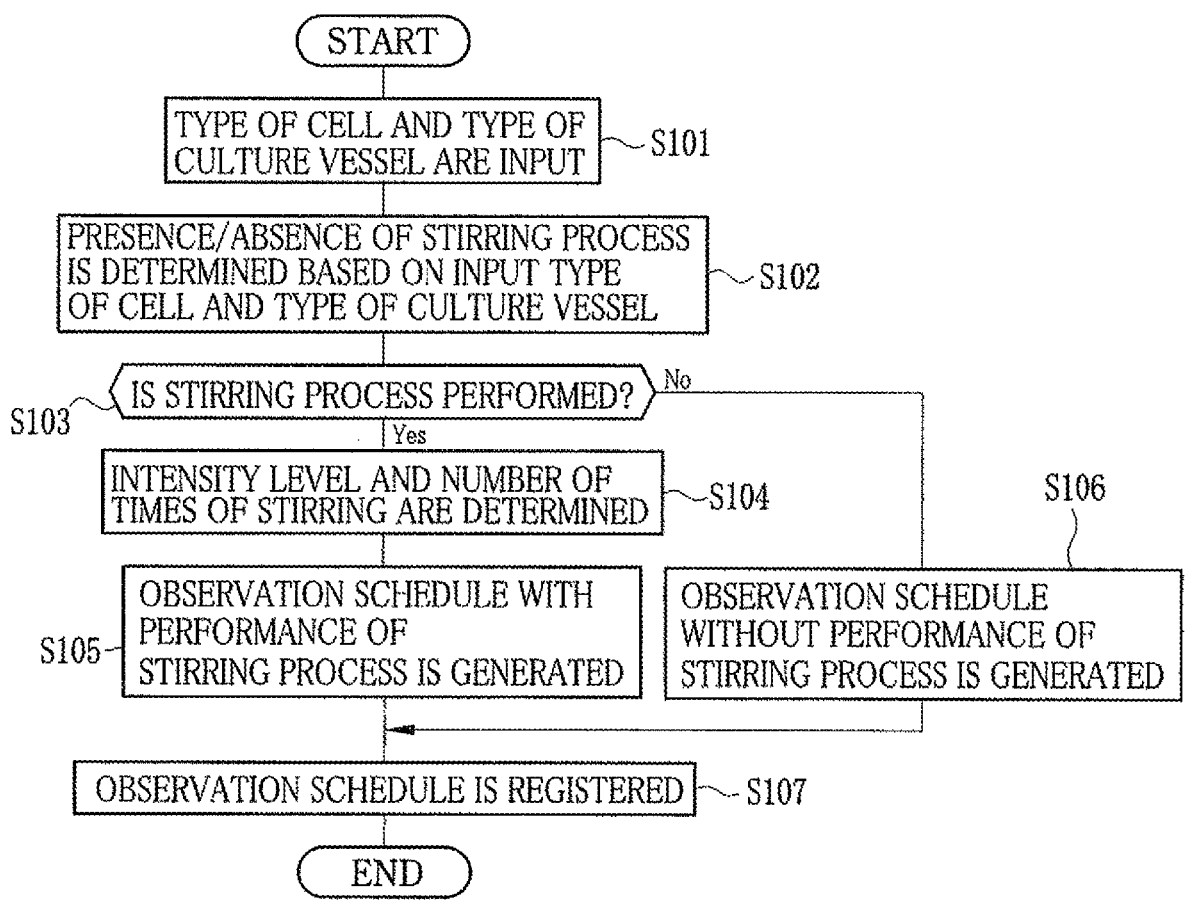
FIG. 6 is a flow chart illustrating a flow of generation and registration of an observation schedule.

Hereinafter, a flow of process of generating and registering the observation schedule will be described based on a flow chart in FIG. 6. Note that FIG. 6 illustrates a flow when the type of the cell to be cultured and the type of the culture vessel 31 used for the culture are previously known.

Step S101 corresponds to a process of inputting the type of the cell and the type of the culture vessel. A user operates the input unit 65b to input the type of the cell and the type of the culture vessel 31. In this case, it is also possible to design such that the type of the cell and the type of the culture vessel 31 can be directly input through the input unit 65b, or a list of types of cells and a list of types of the culture vessels 31 are displayed on the monitor 65a and selection is made through the operation of the input unit 65b.

Step S102 corresponds to a process of determining the presence/absence of the stirring process based on the input type of the cell and type of the culture vessel. In step S101, the type of the cell to be cultured and the type of the culture vessel 31 have been input. The CPU 74 reads the first stirring data 78 stored in the memory 73, and from data corresponding to a combination of the type of the cell and the type of the culture vessel 31 input through the operation of the input unit 65b, it reads information regarding the presence/absence of the stirring process. Based on the read information regarding the presence/absence of the stirring process, it is determined whether the stirring process is actually performed or not.

Step S103 is a step of determining whether or not the stirring process is executed. By executing the process in step S102, the information regarding the presence/absence of the stirring process has been read by the CPU 74. When the read information regarding the presence/absence of the stirring process is information indicating that the stirring process is executed, the CPU 74 sets a result of the determination process in the step S103 to Yes. In this case, the process proceeds to step S104. On the other hand, when the read information regarding the presence/absence of the stirring process is information indicating that the stirring process is not executed, the CPU 74 sets the result of the determination process in the step S103 to No. In this case, the process proceeds to step S106.

Generally, depending on the combination of the cell to be cultured and the culture vessel 31 in which the cell is cultured, there are various cases such that the adhesive strength between the cell and the surface for adhesion when the cell is adhered to the surface for adhesion of the culture vessel 31 that performs the culture becomes lower or greater than the adhesive strength between the cell and the cell when the cell and the cell are connected to each other. For example, when the adhesive strength between the cell and the surface for adhesion when the cell is adhered to the surface for adhesion is lower than the adhesive strength between the cell and the cell when the cells are connected to each other, the cell to be cultured is easily connected to another cell, resulting in that a portion in which a plurality of cells are connected to be aggregated (referred to as an aggregated portion, hereinafter) is generated. In the aggregated portion, the culture solution 33 does not reach the cell inside of the aggregated portion, so that the cell to be cultured dies out. For this reason, when the adhesive strength between the cell and the surface for adhesion when the cell is adhered to the surface for adhesion is lower than the adhesive strength between the cell and the cell when the cells are connected to each other, it is necessary to execute the aforementioned stirring process. In such a case, the CPU 74 makes a determination of Yes in the aforementioned step S103.

On the other hand, when the adhesive strength between the cell and the surface for adhesion when the cell is adhered to the surface for adhesion is greater than the adhesive strength between the cell and the cell when the cell and the cell are connected to each other, the cell becomes easily adhered to the culture vessel 31, and becomes difficult to be connected to another cell. Specifically, if the cells are previously seeded in a uniform manner, each cell deposits without being connected to another cell, and is adhered to the culture vessel 31. When the stirring process is executed in this state, there is a possibility that the cell adhered to the culture vessel 31 is peeled off from the culture vessel 31, and is connected to another cell or is died out without connecting to another cell, so that in such a case, the stirring process is not performed. Specifically, the CPU 74 makes a determination of No in the step S103.

Step S104 corresponds to a process of determining the intensity of stirring and the number of times of stirring in the stirring process. The CPU 74 reads the first stirring data stored in the memory 73, and reads the information regarding the intensity level of stirring, and the number of times of stirring from the data corresponding to the combination of the type of the cell and the type of the culture vessel 31 input through the operation of the input unit 65b. Accordingly, the intensity level of stirring and the number of times of stirring in the stirring process to be actually executed with respect to the culture vessel 31 in which the cell is cultured, are determined from the read information.

Step S105 corresponds to a process of generating an observation schedule with the performance of stirring process. The CPU 74 reads the operation data stored in the memory 73, thereby generating the observation schedule. The CPU 74 makes out a schedule of each process so that the observation process and the medium replacement process are not executed at the same timing as that of the stirring process, to thereby generate the observation schedule. At this time, the CPU 74 generates the schedule of the stirring process included in the observation schedule, based on the intensity level of stirring and the number of times of stirring determined in step S104.

When it is determined that the stirring process is not executed in the determination process in step S103, the process proceeds to step S106. Step S106 corresponds to a process of generating an observation schedule without the performance of stirring process. As the observation schedule without the performance of stirring process, there can be cited a schedule of the aforementioned observation process and medium replacement process and the like.

Step S107 corresponds to a registration process of the observation schedule. The CPU 74 makes the observation schedule generated by executing step S105 or step S106 correspond to the identification number, and then writes the schedule data 76 on which the observation schedule is based, in the memory 73. Note that based on the schedule data 76 written in the memory 73, the observation process and the medium replacement process of the cells cultured in the culture vessel 31 are respectively executed, and the stirring process is executed according to need.

According to the above description, if the combination of the type of the culture vessel 31 and the type of the cell to be cultured is previously known, and further, the first stirring data 78 corresponding to the combination is stored in the memory 73, it is possible to easily determine the presence/absence of the stirring process, and the intensity level and the number of times of stirring in the stirring process when performing the stirring process, and further, it is possible to easily generate the observation schedule in accordance with the combination of the cell to be cultured and the culture vessel 31 to be used. By performing the culture of cells based on the observation schedule, it is possible to prevent the occurrence of density variation of cells proliferated in a process of performing the culture, which enables to efficiently culture the cells.

Some users who perform such culture of cells may culture cells regarding which an adhesive force between the culture vessel 31 and the cell to be cultured and an adhesive force between the mutual cells to be cultured are not yet registered in the first stirring data 78, and thus there is a case where the determination of the stirring process described above cannot be performed even when the input is made through the input unit 65*b*. In order to deal with such a case, for example, the cell culture apparatus of the present embodiment includes a measurement mode in which an adhesive strength between a cell and a cell and an adhesive strength between a cell and a surface for adhesion, for example, of a sample of cells to be actually cultured are determined, and an observation schedule is generated based on these adhesive strengths. Hereinafter, description will be made on a process of generating the observation schedule using the measurement mode, based on a flow chart in FIG. 7.

Step S201 corresponds to a process where the culture vessel 31 is carried in. The user opens each of the carry-in door 22 of the outer door 18*b* and the small door 24 of the inner door 17, and sets the carrier 25 that houses the culture vessel 31 onto the carrier installation cradle 26. After the carrier 25 is set onto the carrier installation cradle 26, the small door 24 of the inner door 17 and the carry-in door 22 of the outer door 18*b* are respectively closed. Note that the culture vessel 31 housed in the carrier 25 is preferably the culture vessel 31 that holds the culture solution 33 including cells for generating the observation schedule.

Step S202 corresponds to a process of transporting the culture vessel to the observation unit. When the carrier 25 is set onto the carrier installation cradle 26, the carrier 25 is detected by a sensor (illustration is omitted) provided to the carrier installation cradle 26. Further, when the carry-in door 22 of the outer door 18*b* and the small door 24 of the inner door 17 are respectively closed, states of the doors are detected by sensors (illustration is omitted) that detect closed states of the respective doors. Upon receiving detection signals from these sensors, the CPU 74 drives the vessel transport mechanism 28 to transport the culture vessel 31 housed in the carrier 25 to the observation unit 30 from the inside of the carrier 25. Accordingly, the culture vessel 31 is placed on a stage 30*a* of the observation unit 30, and positioning of the culture vessel 31 is performed when placing the vessel.

Step S203 corresponds to a process of obtaining images and performing image analysis. The CPU 74 obtains a plurality of slice images with a certain interval therebetween in an optical axis direction (Z direction) via the observation unit 30. Note that, as is generally known, these slice images can be obtained by performing confocal observation. The CPU 74 generates a three-dimensional image of each cell inside of the culture vessel 31 by using these slice images. Accordingly, a state of culture of each cell inside of the culture vessel 31 such that each cell inside of the culture vessel 31 is suspended and each cell is adhered to the culture vessel 31, is identified.

Step S204 corresponds to a process of determining whether or not there is a cell which is point-adhered to the culture vessel. By the process of step S203, the states of culture of cells inside of the culture vessel 31 have been identified. The CPU 74 determines whether or not there is a point-adhered cell among the identified respective cells, based on a result of identification in step S203. Hereinafter, a case where one cell is point-adhered to the culture vessel 31 will be described, for the sake of convenience. For example, when there is a point-adhered adhered cell 91, the CPU 74 sets a result of the determination process in the step S204 to Yes, and the process proceeds to step S206. When the determination process is performed, the CPU 74 writes a position of the point-adhered adhered cell 91 (X-coordinate, Y-coordinate) into the memory 73. At the same time, the CPU 74 specifies a suspended cell 90, and also writes a position of the suspended cell 90 into the memory 73. On the other hand, when there is no point-adhered adhered cell 91, the CPU 74 sets the result of the process in the step S204 to No. In this case, the process proceeds to step S205.

Step S205 corresponds to a process of determining whether or not a waiting time has elapsed. The CPU 74 counts an elapsed time after the execution of the determination process in step S205, and determines whether or not the time has reached the waiting time. Note that the waiting time is a period of time shorter than the fixing time, and is 10 minutes, for example. For example, when the CPU 74 determines that the waiting time has elapsed, the CPU 74 sets a result of the determination process in the step S205 to Yes, and the process proceeds to step S206. On the other hand, when it is determined that a given period of time has not elapsed, the CPU 74 sets the result of the determination process in the step S205 to No. In this case, the process in step S205 is repeatedly executed.

Figure 8A:
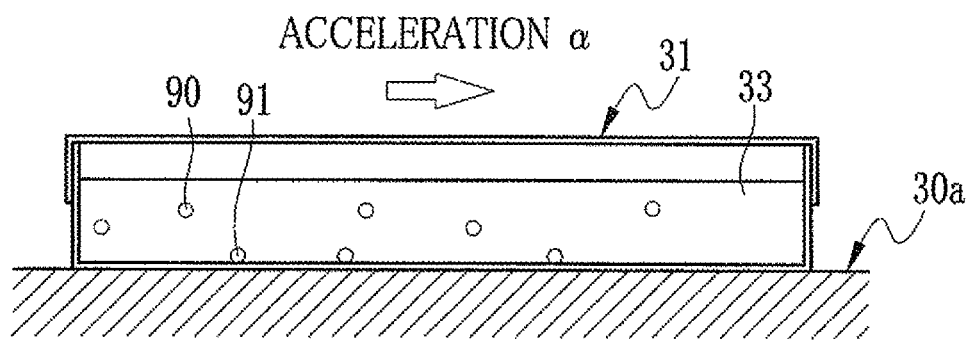
FIG. 8A is a diagram illustrating a state of culture vessel immediately before a stage of an observation unit is transported at an acceleration α.
Figure 8B:
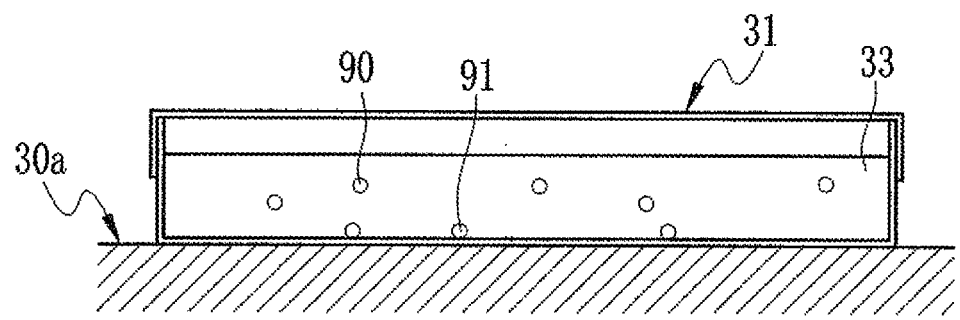
FIG. 8B is a diagram illustrating a state of culture vessel after the stage transported at the acceleration α is stopped.

Step S206 corresponds to a process of measuring the adhesive strength between the cell and the surface for adhesion. First, the CPU 74 drives the observation unit 30 to transport the stage 30*a* of the observation unit 30 at an acceleration $\alpha$ (refer to FIG. 8A), and stops the stage 30*a* (refer to FIG. 8B). When the stage is stopped and when a given period of time t has elapsed after stopping the stage, the CPU 74 makes the observation unit 30 obtain entire images of the culture vessel 31. The CPU 74 calculates, based on the obtained two entire images, respective moving distances of the suspended cell 90 and the adhered cell 91 specified by executing step S203. Hereinafter, description will be made by giving a reference numeral 90 to the suspended cell, a reference numeral 91 to the adhered cell, and a reference numeral 92 to the surface for adhesion. After the calculation of these moving distances, an ease of peeling of the adhered cell 91 is determined. Concretely, the peeled-off cell moves at a certain speed by an acceleration α' as a result of subtracting an amount of acceleration consumed for peeling off the cell from the acceleration given to the adhered cell 91. Therefore, if the moving distance is large, it can be understood that the adhesive strength is small, and the cell is easily peeled off. Further, on the contrary, if the moving distance is small, it can be understood that the adhesive strength is large, and the cell is difficult to be peeled off. Conclusively, the adhesive strength between the cell and the surface for adhesion is estimated. Note that the index α' regarding the acceleration is an acceleration given to the cell point-adhered to the culture vessel 31 for peeling off from the culture vessel 31, regardless of the type of cells. The acceleration α' is a value which can be previously estimated through experiments, researches, statistics and the like. Further, the index α' regarding the acceleration becomes one of indexes indicating the adhesive strength between the cell and the culture vessel 31.

Figure 9:
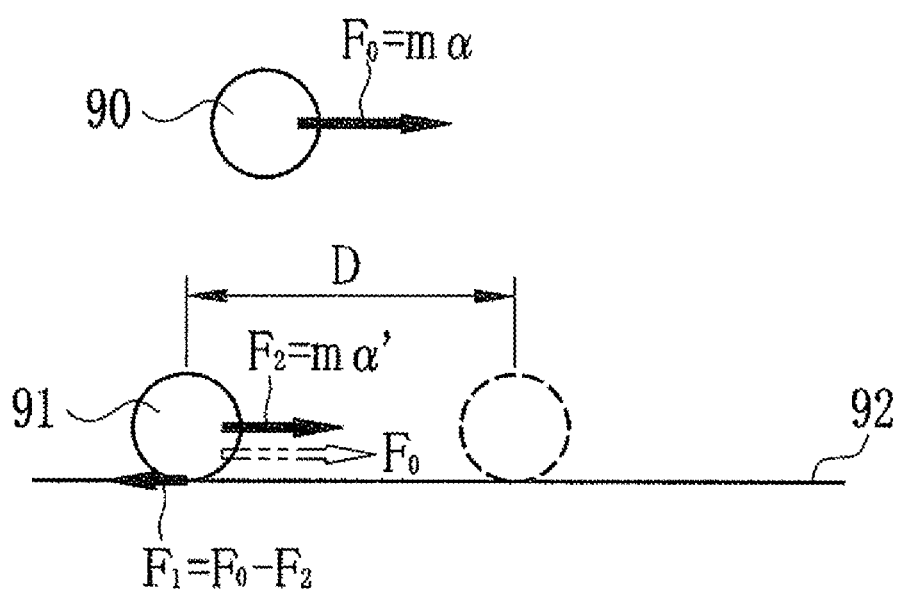
FIG. 9 is a diagram illustrating a movement of suspended cell and a movement of adhered cell point-adhered to a surface for adhesion when the stage transported at the acceleration α is stopped.

As illustrated in FIG. 9, if a mass of each of the suspended cell 90 inside of the culture vessel 31 and the adhered cell 91 point-adhered to the surface for adhesion 92 is set to m, and when the stage 30a is transported at the acceleration α and then the stage 30a is stopped, an external force $F_0$ ($=m\alpha$) due to the acceleration α acts on the suspended cell 90. Meanwhile, on the point-adhered adhered cell 91, the same external force $F_0$ as that on the suspended cell 90 acts, and in addition to that, an adhesive force $F_1$ generated between the cell and the surface for adhesion acts in a direction opposite to the direction of the external force $F_0$. For this reason, a force of $F_0-F_1$ ($=F_2$) acts on the point-adhered adhered cell 91, and by the force, the adhered cell 91 is peeled off from the surface for adhesion 92. The acceleration with respect to the adhered cell 91 peeled off at this time is set to α' (α'<α). For example, a moving distance D of the adhered cell 91 and a speed of the adhered cell 91 from when the stage 30a is stopped to when the given period of time t elapses can be roughly determined from the obtained images or coordinate values of respective cells specified from the images, so that from these values, it is possible to calculate the index α' regarding the acceleration similar to the acceleration generated with respect to the peeled-off adhered cell 91. By calculating the index α' regarding the acceleration, the force $F_2$ that acts on the peeled-off adhered cell 91 is calculated. By calculating the force $F_2$, the adhesive force $F_1$ between the cell and the surface for adhesion is determined as the adhesive strength between the cell and the surface for adhesion.

Step S207 corresponds to a process of determining whether or not the fixing time has elapsed. When the step S207 is executed, the CPU 74 starts counting of time. When the time counted by the CPU 74 reaches the fixing time, the CPU 74 determines that the fixing time has elapsed. In this case, a result of the determination process in the step S207 is set to Yes, and the process proceeds to step S208. On the other hand, when the time has not reached the fixing time, the CPU 74 sets the result of the determination process in the step S207 to No, and repeatedly executes the process in the step S207 until the time reaches the fixing time.

Step S208 corresponds to a process of calculating the adhesive strength between the cell and the cell. First, the CPU 74 drives the observation unit 30 to obtain an entire image of the culture vessel 31. The CPU 74 performs image analysis using the obtained entire image of the culture vessel 31, and specifies an aggregated portion generated when a plurality of cells are connected.

For specifying the aggregated portion, a binarization process is first performed on the obtained entire image of the culture vessel 31. The binarization process is a process in which a luminance value exceeding a previously set threshold value and a luminance value which is equal to or less than the threshold value are divided into two values. Accordingly, it becomes possible to classify a region indicating a contour of the culture vessel 31 and a region of the aggregated portion, and the other regions, for example. Note that the contour of the culture vessel 31 is previously known, so that after the binarization process, the region indicating the contour of the culture vessel 31 is deleted. After these processes, a region with a predetermined size or more is specified as the aggregated portion. Note that the CPU 74 stores a position (X-coordinate, Y-coordinate) of the specified aggregated portion in the memory 73. Hereinafter, description will be made by giving a reference numeral 95 to the aggregated portion, and a reference numeral 96 to each of adhered cells that form the aggregated portion 95.

After these processes, the stage 30a of the observation unit 30 is transported at the acceleration α, and then the stage 30a which is being transported is stopped, in a similar manner to that of the process in step S208. Also at this time, entire images of the culture vessel 31 are obtained when the stage 30a is stopped and when a predetermined period of time t has elapsed after stopping the stage 30a, respectively, in a similar manner.

Figure 10:
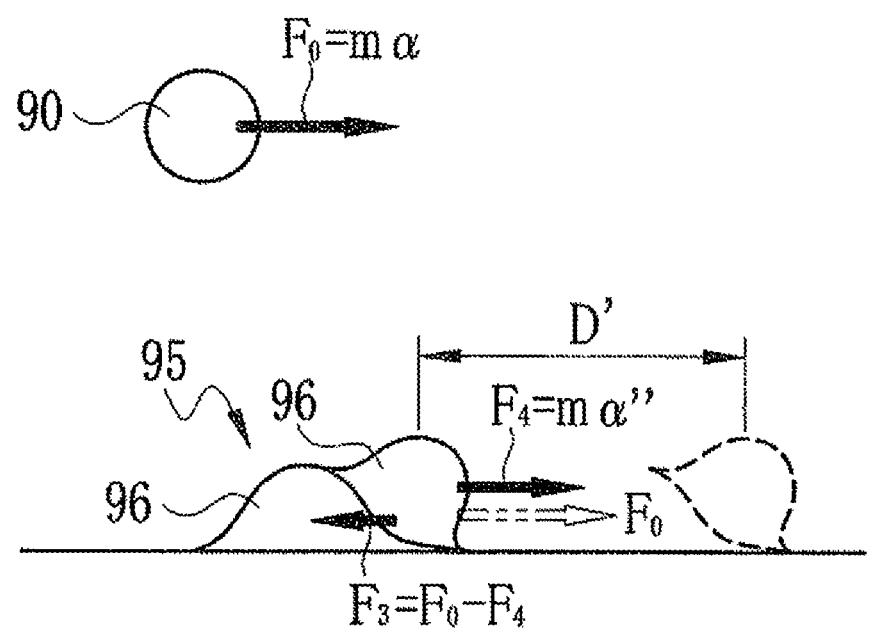
FIG. 10 is a diagram illustrating a movement of suspended cell and a movement of adhered cell connected to another adhered cell when the stage transported at the acceleration α is stopped.

By drive-controlling the stage 30a, the acceleration α is applied to each of the adhered cells 96 connected as the aggregated portion 95, and respective adhered cells 96 are peeled off. As illustrated in FIG. 10, on the adhered cell 96, the same external force $F_0$ as that on the suspended cell 90 acts, and in addition to that, an adhesive force $F_3$ generated between the cell and the cell acts in a direction opposite to the direction of the external force $F_0$. For this reason, a force of $F_0-F_3$ ($=F_4$) acts on the adhered cell 96 connected to another adhered cell 96 in the aggregated portion 95, and by the force, the adhered cell 96 is peeled off from another adhered cell 96 in the aggregated portion 95. An index regarding the acceleration generated with respect to the adhered cell 96 peeled off at this time is set to α" (α"<α). For example, a moving distance D' of the adhered cell 96 and a speed of the adhered cell 96 from when the stage 30a is stopped to when the period of time t elapses can be determined from the obtained entire images, so that from these values, it is possible to calculate the index α" regarding the acceleration with respect to the peeled-off adhered cell 96. By calculating the index α" regarding the acceleration, the force $F_4$ that acts on the peeled-off adhered cell 96 is calculated. By calculating the force $F_4$ that acts on the peeled-off adhered cell 96, the adhesive force $F_3$ between the cell and the cell is determined as the adhesive strength between the cell and the cell.

Step S209 corresponds to a process of determining the presence/absence of the stirring process based on the determined adhesive strengths. By executing the process in step S206, the adhesive strength $F_1$ between the cell and the surface for adhesion is determined, and by executing the process in step S208, the adhesive strength $F_3$ between the cell and the cell is determined. The CPU 74 reads the second stirring data 79 from the memory 73, and determines the presence/absence of the stirring process based on the adhesive strength $F_1$ between the cell and the surface for adhesion, the adhesive strength $F_3$ between the cell and the cell and the second stirring data 79. For example, if the adhesive strength $F_1$ between the cell and the surface for adhesion becomes smaller than the adhesive strength $F_3$ between the cell and the cell, the aggregated portion 95 is generated in a process of culturing the cells, so that the CPU 74 sets that the stirring process is performed (presence of stirring process). On the other hand, if the adhesive strength $F_1$ between the cell and the surface for adhesion becomes larger than the adhesive strength $F_3$ between the cell and the cell, the aforementioned aggregated portion 95 is not generated in a process of culturing the cells, so that the CPU 74 sets that the stirring process is not performed (absence of stirring process).

Step S210 corresponds to a process of determining whether or not there exists the stirring process. When "presence of stirring process" is set in the process in step S209, the CPU 74 sets a result of the determination process in the step S210 to Yes, and the process proceeds to step S211. On the other hand, when "absence of stirring process" is set in the process in step S209, the CPU 74 sets a result of the determination process in the step S210 to No, and the process proceeds to step S213.

Step S211 corresponds to a process of determining the intensity level and the number of times of stirring in the stirring process. Note that the process in the step S211 is similar to the process in step S104, so that details thereof will be omitted. Note that in the step S210, the CPU 74 refers to the second stirring data 79 to determine the intensity level and the number of times of stirring in the stirring process.

Step S212 corresponds to a process of generating the observation schedule with the performance of stirring process. The process in the step S212 is similar to the process in step S105, so that details thereof will be omitted here.

Step S213 corresponds to a process of generating the observation schedule without the performance of stirring process. The process in the step S213 is similar to the process in step S106, so that details thereof will be omitted here.

Step S214 corresponds to a process of registering the generated observation schedule. The process in the step S214 is similar to the process in step S107, so that details thereof will be omitted here. Accordingly, even when the type of the cell and the type of the culture vessel 31 to be used are not previously known, by measuring the adhesive strength between the cell and the cell and the adhesive strength between the cell and the surface for adhesion, the presence/absence of the stirring process, and the intensity level and the number of times of stirring in the stirring process when performing the stirring process, are automatically determined, and then the observation schedule based on the determined content is generated. By culturing cells based on the generated observation schedule, it is possible to prevent the seeding variation that occurs in a process of performing the culture, and the occurrence of density variation of cells proliferated in a process of performing the culture, which enables to efficiently culture the cells.

Note that in the present embodiment, the observation schedule is generated by using the measurement mode when the type of the cell and the type of the culture vessel 31 to be used are not known, but, there are cases in which, for example, even when the type of the cell and the culture vessel 31 used for the culture are known, a combination of these is not registered in the first stirring data 78, and intended cells are wanted to be cultured after reconfirming whether or not the aggregated portion 95 is actually generated. In such cases, it is also possible to design such that the aforementioned measurement mode can be executed after inputting a type of cell and a culture vessel to be used. This enables to deal with a case where, even with a combination of the type of the cell and the type of the culture vessel with which the observation schedule with no performance of stirring process is generated in the previously registered data, the aggregated portion 95 is generated at the time of actually performing the culture, and the like. In such a case, it is only required that the CPU 74 refers to the second stirring data 79 without using the first stirring data to determine the presence/absence of the stirring process and to determine the intensity level and the number of times of stirring when performing the stirring process, thereby generating the observation schedule.

In the present embodiment, by inputting the type of the cell and the type of the culture vessel 31 to be used, the presence/absence of the stirring process, and the intensity level and the number of times of stirring in the stirring process when performing the stirring process, are determined. Among the culture vessels 31 used at the time of actually culturing the cells, there is one whose surface for adhesion is subjected to special surface treatment. In order to allow the use of such culture vessel 31, to the information input through the input unit 65b, a type of surface treatment on the culture vessel 31 may also be added, in addition to the type of the cell and the type of the culture vessel. In this case, it is also possible to design such that the input is directly made through the input unit 65b or the selection can be made from a list.

In the present embodiment, the adhesive strength (adhesive force) between the cell and the cell and the adhesive strength (adhesive force) between the cell and the surface for adhesion are determined, but, there is no need to limit to this, and it is only required to detect a magnitude relation of the ease of peeling by giving an external force to the cells adhered to the inner surface of the culture vessel and another cultured cell. Further, it is not necessarily required to correctly determine the strength and the acceleration after the cell is peeled off, and it is only required to determine an index by which the adhesive strength between the cell and the inner surface of the culture vessel or the adhesive strength between mutual cells can be analogized (estimated). For example, it is also possible that a ratio between the moving distance of the suspended cell and the moving distance of the peeled-off adhered cell, and a ratio between the moving distance of the suspended cell and the moving distance of the adhered cell peeled off from the aggregated portion, are determined, the ratios are handled as indexes regarding the adhesive strengths, it is determined whether or not the stirring process is executed, and the intensity level and the number of times of stirring in the stirring process are determined when executing the stirring process, based on these ratios, and then the observation schedule is generated. Further, other than this, it is also possible that a ratio between the speed of the suspended cell and the speed of the peeled-off adhered cell, and a ratio between the speed of the suspended cell and the speed of the adhered cell peeled off from the aggregated portion, are determined, it is determined whether or not the stirring process is executed, and the intensity level and the number of times of stirring in the stirring process are determined when executing the stirring process, based on these ratios, and then the observation schedule is generated.

In the present embodiment, the cell to be a target when calculating the adhesive strength between the cell and the surface for adhesion and the adhesive strength between the cell and the cell is set to one cell, but, there is no need to limit to this, and a plurality of cells may also be set as targets. In this case, as the aforementioned adhesive strength, an average value of the adhesive strengths calculated for respective cells may be determined.

Figure 7:
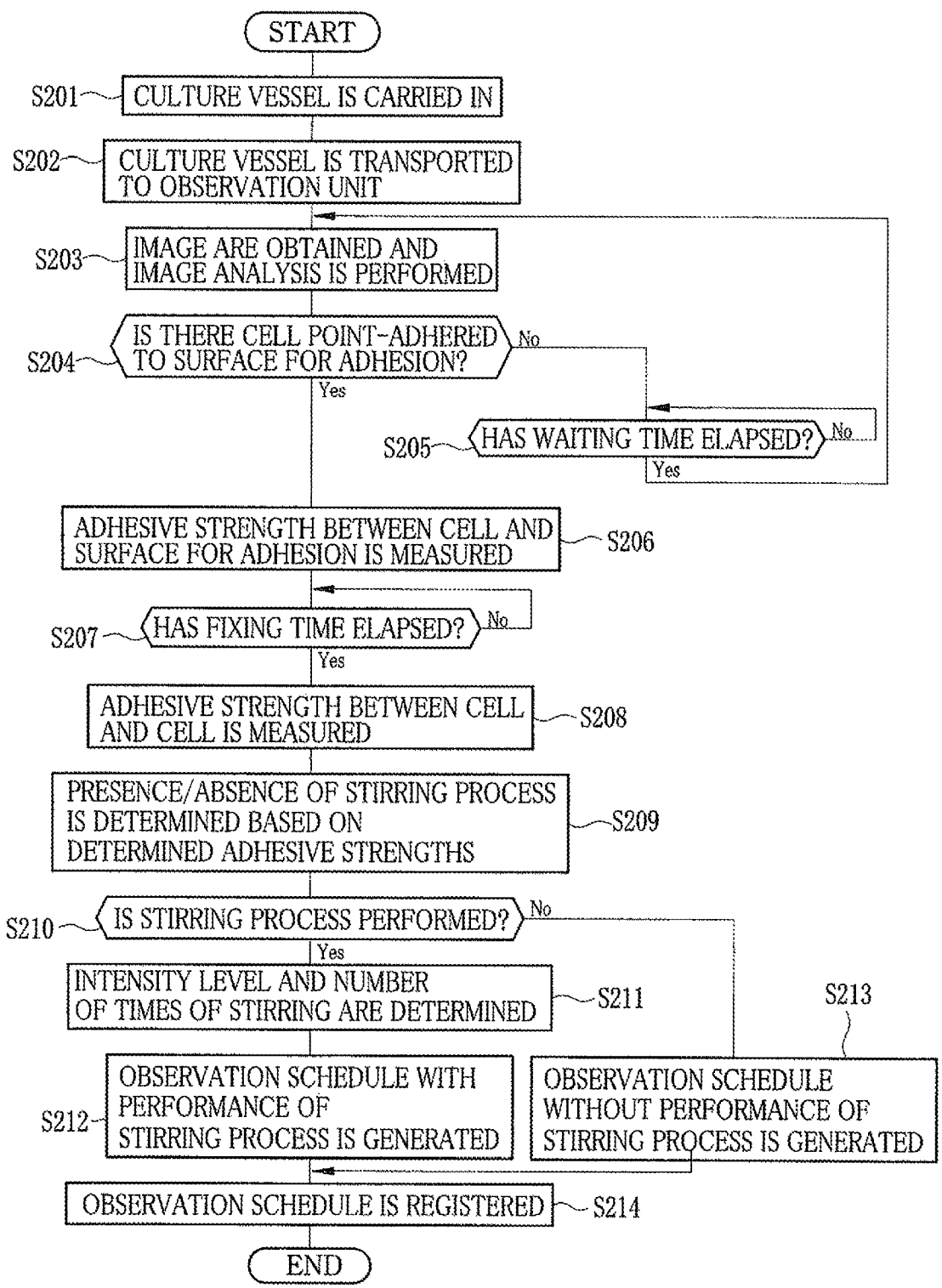
FIG. 7 is a flow chart illustrating a flow of generation and registration of an observation schedule using a measurement mode.

In the present embodiment, the cell culture apparatus that cultures cells is adopted as an example, but, there is no need to limit to this, and it is also possible to adopt a program for making the CPU of the cell culture apparatus execute the functions of the image analyzing section 81, the operating section 82, the schedule management section 83 and the timer 84 illustrated in FIG. 5, and the function of the flow charts illustrated in FIG. 6 and FIG. 7. In this case, when the program is installed in the cell culture apparatus, there is a need to write the operation data 77, the first stirring data 78, and the second stirring data 79 into the memory and the database section. Note that the aforementioned program and data are preferably stored in a storage medium such as a memory card, an optical disk, a magnetic disk or the like, for example.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A stirring apparatus comprising:
   a stirring mechanism (i) comprising a movable stage, on which a culture vessel containing cells is placed, and (ii) being configured to execute a stirring process in which a predetermined vibration is applied to the culture vessel according to at least one of an intensity of stirring and a number of times of stirring on the cells in the culture vessel, the stirring process being (i) a process of releasing an adhesion state between the culture vessel and a cell of the cells in the culture vessel or (ii) a process of releasing an adhesion state between mutual cells of the cells in the culture vessel; and
   a control unit including a central processor unit (CPU) to which are connected a memory and the stirring mechanism, the memory containing a program indicating to the CPU a procedure for the stirring process of the stirring mechanism,
   wherein the memory stores, in accordance with the type of the culture vessel and the type of the cells in the culture vessel, adhesive strength data corresponding to (i) a first adhesive strength between the cell and an inner surface of the culture vessel and (ii) a second adhesive strength between the mutual cells, and
   the CPU is programmed to execute the procedure for the stirring process, the procedure comprising:
      reading the adhesive strength data corresponding to the first adhesive strength and the second adhesive strength from the memory when the type of the cells and the type of the culture vessel are input through operation of an input unit,
      determining whether the stirring process of the stirring mechanism is to be executed or not based on a combination of (i) the type of the cells, (ii) the type of the culture vessel, and (iii) the adhesive strength data read from the memory when the type of the cells and the type of the culture vessel are input,
      determining the intensity of stirring and the number of times of stirring in the stirring process based on the combination of (i) the type of the cells, (ii) the type of the culture vessel, and (iii) the adhesive strength data read from the memory when the stirring process of the stirring mechanism is determined, and
      causing the stirring mechanism to execute the stirring process by controlling of the stirring mechanism based on at least one of the determined intensity of stirring and the determined number of times of stirring in accordance with a result of determining whether the stirring process is to be executed or not.

2. The stirring apparatus according to claim 1, wherein the movable stage includes at least one of an X stage, a Y stage, and a rotation stage,
   the memory further stores a magnitude relation between the first adhesive strength and the second adhesive strength, and
   the determining whether the stirring process is to be executed or not is further based on the magnitude relation.

3. A stirring apparatus comprising:
   a stirring mechanism (i) comprising a movable stage, on which a culture vessel containing cells is placed, and (ii) being configured to execute a stirring process in which a predetermined vibration is applied to the culture vessel according to at least one of a an intensity of stirring and a number of times of stirring on the cells in the culture vessel, the stirring process being (i) a process of releasing an adhesion state between the culture vessel and a cell of the cells in the culture vessel or (ii) a process of releasing an adhesion state between mutual cells of the cells in the culture vessel;
   an observation unit comprising a microscope and being configured (i) to perform observation from a predetermined movement given to the movable stage and (ii) to obtain during the observation a plurality of images of the cells in the culture vessel or of the culture vessel; and
   a control unit comprising a communication section and a central processor unit (CPU) connected to the stirring mechanism and the observation unit, the control unit being programmed to control the stirring mechanism and the observation unit based on a process content of the stirring process,
   wherein the control unit:
      calculates, based on the plurality of images, (i) an adhesive strength between the cell of the cells in the culture vessel and an inner surface of the culture vessel and (ii) an adhesive strength between the mutual cells,
      determines, in accordance with the type of the culture vessel and the type of the cells in the culture vessel and when the type of the culture vessel and the type of the cells are received by the control unit, the process content of the stirring process based on a magnitude relation between (i) the calculated adhesive strength between the cell and the inner surface of the culture vessel and (ii) the calculated adhesive strength between the mutual cells, the process content indicating to the CPU (i) whether the stirring process is to be executed or not, (ii) the intensity of stirring according to the stirring process, and (iii) the number of times of stirring applied to the culture vessel, and
      when the process content indicates that the stirring process is to be executed, causes the stirring mechanism to execute the stirring process on the cells in the culture vessel by controlling the stirring mechanism based on at least one of the intensity of stirring indicated by the process content and the number of times of stirring indicated by the process content.

4. The stirring apparatus according to claim 3, wherein the control unit stores the magnitude relation.

5. A cell culture apparatus, comprising:
the stirring apparatus according to claim 1; and
a temperature-controlled room including the stirring apparatus in an inside thereof and configured to maintain an environment at a state of culturing the cells.

6. A cell culture apparatus, comprising:
the stirring apparatus according to claim 3; and
a temperature-controlled room including the stirring apparatus in an inside thereof and configured to maintain an environment at a state of culturing the cells.

7. A stirring method comprising:
controlling a control unit including a central processor unit (CPU) configured
to drive a stirring mechanism comprising a movable stage, on which a culture vessel containing cells is placed, and
to perform a stirring process in which a predetermined vibration is applied to the culture vessel according to at least one of an intensity of stirring and a number of times of stirring on the cells in the culture vessel, the stirring process being (i) a process of releasing an adhesion state between the culture vessel and a cell of the cells in the culture vessel or (ii) a process of releasing an adhesion state between mutual cells of the cells in the culture vessel;

reading, from a memory connected to the control unit and in accordance with the type of the cells in the culture vessel and the type of the culture vessel, adhesive strength data corresponding to (i) a first adhesive strength between the cell and an inner surface of the culture vessel and (ii) a second adhesive strength between the mutual cells, when the type of the cells and the type of the culture vessel are input through operation of an input unit, the memory containing a program indicating to the CPU a procedure of the stirring process of the stirring mechanism;

determining whether the stirring process of the stirring mechanism is to be executed or not based on a combination of (i) the type of the cells, (ii) the type of the culture vessel, and (iii) the adhesive strength data corresponding to the first adhesive strength and the second adhesive strength read from the memory;

determining the intensity of stirring and the number of times of stirring in the stirring process based on the combination of (i) the type of the cells, (ii) the type of the culture vessel, and (iii) the adhesive strength data corresponding to the first adhesive strength and the second adhesive strength read from the memory when the stirring process of the stirring mechanism is determined; and executing the stirring process by controlling the stirring mechanism based on at least one of the determined intensity of stirring and the determined number of times of stirring.

* * * * *